(12) United States Patent
Nagano et al.

(10) Patent No.: US 8,394,850 B2
(45) Date of Patent: Mar. 12, 2013

(54) FLUORESCENT PROBE SPECIFIC TO HYDROGEN PEROXIDE

(75) Inventors: Tetsuo Nagano, Tokyo (JP); Yasuteru Urano, Kanagawa (JP); Masahiro Abo, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 12/920,684

(22) PCT Filed: Mar. 4, 2009

(86) PCT No.: PCT/JP2009/054017
§ 371 (c)(1),
(2), (4) Date: Jan. 28, 2011

(87) PCT Pub. No.: WO2009/110487
PCT Pub. Date: Sep. 11, 2009

(65) Prior Publication Data
US 2011/0159603 A1 Jun. 30, 2011

Related U.S. Application Data

(60) Provisional application No. 61/033,511, filed on Mar. 4, 2008.

(51) Int. Cl.
*A61K 31/352* (2006.01)
*C07D 311/82* (2006.01)

(52) U.S. Cl. ........ 514/454; 549/356; 549/391; 514/449; 514/453

(58) Field of Classification Search .............. 549/200, 549/356, 388, 391; 514/449, 453, 454
See application file for complete search history.

(56) References Cited

U.S. PATENT DOCUMENTS

| | | | |
|---|---|---|---|
| 4,578,499 A | 3/1986 | Imai et al. | |
| 6,903,226 B2 * | 6/2005 | Nagano et al. | 549/391 |
| 7,074,823 B2 * | 7/2006 | Nagano et al. | 514/453 |
| 7,087,766 B2 | 8/2006 | Nagano et al. | |
| RE40,572 E * | 11/2008 | Nagano et al. | 549/391 |
| 7,491,832 B2 | 2/2009 | Maeda et al. | |
| 7,524,974 B2 * | 4/2009 | Nagano et al. | 549/224 |
| 7,868,147 B2 * | 1/2011 | Nagano et al. | 536/18.1 |
| 2003/0153027 A1 | 8/2003 | Nagano et al. | |
| 2006/0105410 A1 | 5/2006 | Maeda et al. | |

FOREIGN PATENT DOCUMENTS

| | | |
|---|---|---|
| JP | 61-015864 A | 1/1986 |
| JP | 2005-047898 A | 2/2005 |
| WO | 01/64664 A1 | 9/2001 |

OTHER PUBLICATIONS

Nobuaki Soh, "Recent advances in fluorescent probes for the detection of reactive oxygen species", Anal Bioanal Chem, 2006, 386, , pp. 532-543.

H. W. Yurow et al., "Structure chemiluminescence correlations for various organic compounds with luminol-peroxide", Analytica Chimica Acta, 1977, 88, pp. 389-394.
"Abstracts of 128th Annual Meeting of Pharmaceutical Society of Japan", 26M-pm15, Mar. 5, 2008, pp. 11.
"Biophysics", The Biophysical Society of Japan, vol. 48, Supplement 1, Oct. 25, 2008, pp. S177, 3P-321.
International Search Report for PCT/JP2009/054017, in English and Japanese.
International Preliminary Report on Patentability for PCT/JP2009/054017, in English and Japanese.

* cited by examiner

*Primary Examiner* — Golam M M Shameem
(74) *Attorney, Agent, or Firm* — Greenblum & Bernstein, P.L.C.

(57) ABSTRACT

A compound represented by the following general formula (IA) or (IB) ($R^1$ represents an electron withdrawing substituent, $R^2$ and $R^3$ represent a hydrogen atom or a halogen atom; $R^4$ and $R^5$ represent a hydrogen atom, an alkylcarbonyl group, or an alkylcarbonyloxymethyl group, and $R^6$ represents a hydrogen atom or an alkyl group) or a salt thereof, and a reagent for measuring hydrogen peroxide comprising the compound or a salt thereof.

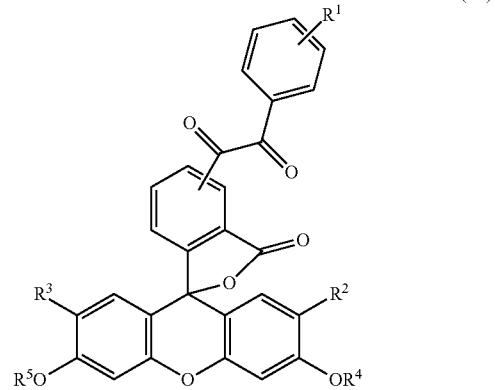

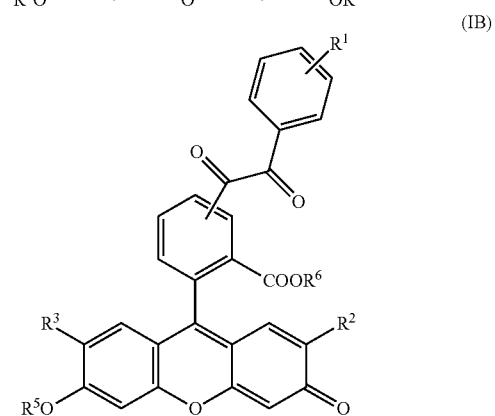

5 Claims, 2 Drawing Sheets

(A)

(B)

(C)

(A)

(B)

FLUORESCENT PROBE SPECIFIC TO HYDROGEN PEROXIDE

TECHNICAL FIELD

The present invention relates to a fluorescent probe which specifically reacts with hydrogen peroxide.

BACKGROUND ART

Hydrogen peroxide is known for many years as a factor toxic to living organisms. However, in recent years, it is thought that reactive oxygen species having comparatively weak oxidizing power, such as superoxide and hydrogen peroxide, are used as signal transduction factors in living organisms. In order to visualize behaviors of hydrogen peroxide in living organisms, a means for specifically visualize hydrogen peroxide is desired. However, although a fluorescent probe that reacts with reactive oxygen species including hydrogen peroxide is known so far (Patent document 1), any fluorescent probe that specifically reacts with hydrogen peroxide and does not substantially react with the other reactive oxygen species has not been developed.
Patent document 1: Japanese Patent Application No. 2004-200921.

DISCLOSURE OF THE INVENTION

Object to be Achieved by the Invention

An object of the present invention is to provide a fluorescent probe that specifically reacts with hydrogen peroxide.

Means for Achieving the Object

The inventors of the present invention conducted various researches in order to achieve the aforementioned object, and as a result, found that the compounds represented by the following general formula (I) reacted with hydrogen peroxide to give marked increase of fluorescence intensity, whilst they did not substantially have reactivity to the other reactive oxygen species (hydroxyl radical, peroxynitrite, hypochlorite ion, superoxide, nitrogen monoxide, singlet oxygen) and did not show increase of fluorescence intensity. The present invention was accomplished on the basis of the above finding.

The present invention thus provides a compound represented by the following general formula (IA) or (IB):

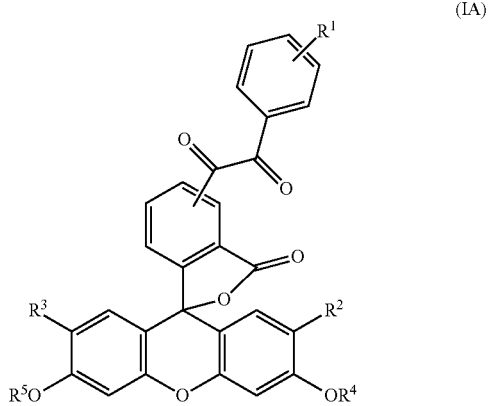
(IA)

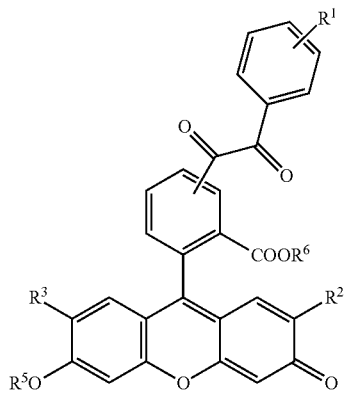
(IB)

(wherein, in the formulae, $R^1$ represents one or two or more electron withdrawing substituents existing on the benzene ring, $R^2$ and $R^3$ independently represent a hydrogen atom or a halogen atom; $R^4$ and $R^5$ independently represent a hydrogen atom, an alkylcarbonyl group, or an alkylcarbonyloxymethyl group, and $R^6$ represents a hydrogen atom or an alkyl group) or a salt thereof.

According to preferred embodiments of the aforementioned invention, there are provided the aforementioned compound or a salt thereof, wherein $R^1$ represents one cyano group, halogen atom, carboxy group, or sulfo group on the benzene ring, $R^2$ and $R^3$ are hydrogen atoms, $R^4$ and $R^5$ are hydrogen atoms, and $R^6$ is a hydrogen atom; and the aforementioned compound or a salt thereof, wherein, in the benzene ring bound to the xanthene ring, the binding position of the dicarbonyl group to which the phenyl group having at least one substituent $R^1$ binds is the para-position to the xanthene ring.

As another aspect, the present invention provides a reagent for measuring hydrogen peroxide, which comprises a compound represented by the aforementioned general formula (IA) or (IB) or a salt thereof. This reagent is useful as a hydrogen peroxide-specific fluorescent probe.

As still another aspect, the present invention provides a method for measuring hydrogen peroxide, which comprises the following steps: (A) reacting the aforementioned reagent with hydrogen peroxide, and (B) measuring fluorescence of a decomposition product of the aforementioned reagent generated in the aforementioned step (A).

Effect of the Invention

The reagent for measuring hydrogen peroxide provided by the present invention has a property that the reagent specifically reacts with hydrogen peroxide among the various active oxygen species to emit strong fluorescence, and thus has a superior characteristic to achieve specific measurement of hydrogen peroxide with high sensitivity.

BRIEF DESCRIPTION OF THE DRAWINGS

FIG. 1.(A) shows the change of a fluorescence spectrum (excitation wavelength: 490 inn) over time observed when hydrogen peroxide ($H_2O_2$, 100 μM) was added to Compound 5 (1 μM); FIG. 1(B) shows relative fluorescence intensities at 520 nm (excitation wavelength: 490 nm) observed when hydrogen peroxide (100 μM, for 30 minutes), hydroxyl radical (10 µM), peroxynitrite (10 µM), hypochlorite ion (10 µM), NOC13 (100 µM) as a nitrogen monoxide generator, and 3-(1,4-dihydro-1,4-epidioxy-1-naphthyl)propionic acid (EP-1, 100 µM) as a singlet oxygen generator were added to Compound 5 (1 µM), respectively; and FIG. 1(C) shows relative fluorescence intensities at 520 nm (excitation wavelength: 490 nm) observed when superoxide (10 µM) was reacted with Compound 5 (10 µM) using a hypoxanthine/xanthine oxidase (HPX/xanthine oxidase (KW) system.

Figure 1:
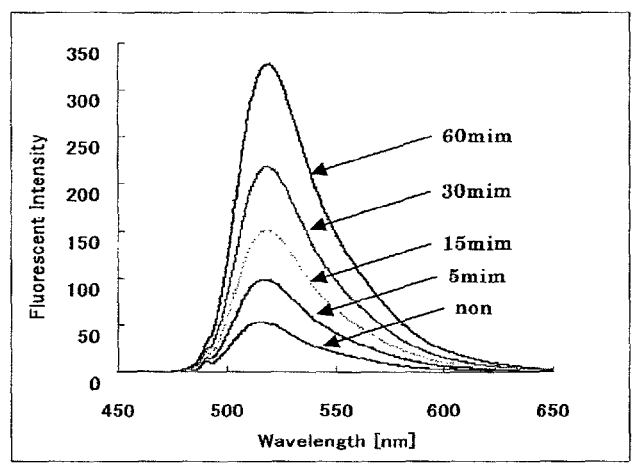
FIG. 1 (A), FIG. 1 (B) and FIG. 1 (C) show characteristics of the reagent for measuring hydrogen peroxide of the present invention.
Figure 1:
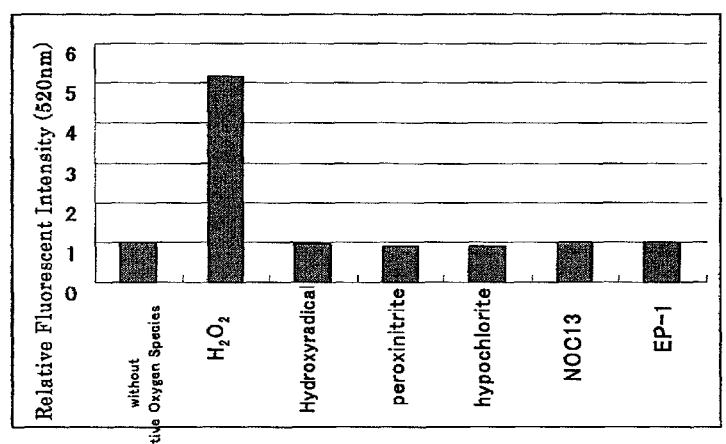
Figure 1:
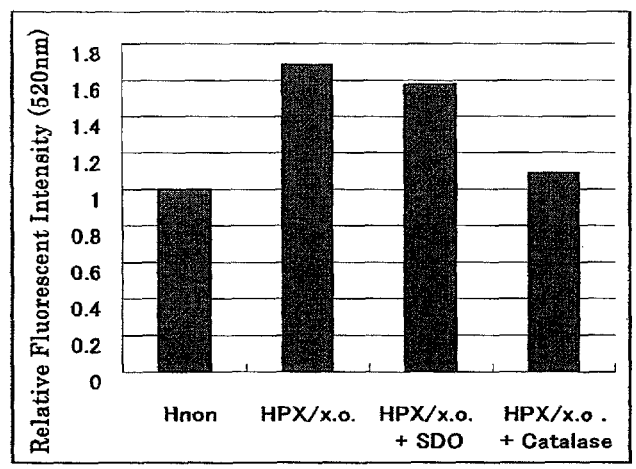

BEST MODE FOR CARRYING OUT THE INVENTION $R^1$ represents one or two or more, and preferably one, electron withdrawing substituent existing on the benzene ring. Type of the electron withdrawing substituent is not particularly limited. Examples include a halogen atom (fluorine atom, chlorine atom, bromine atom, or iodine atom), cyano group, carboxy group, sulfo group, and the like, but it is not limited to these. As $R^1$, for example, cyano group is preferred. On the benzene ring, one or two or more of such substituents $R^1$s can exist, and when two or more of such substituents exist, they may be the same or different. Although the binding position of $R^1$s are not particularly limited, when only one substituent $R^1$ is present, the substituent $R^1$ is preferably in the para-position to the dicarbonyl group. So long as the electron withdrawing property of $R^1$ is not degraded, one or two or more substituents other than $R^1$ (for example, electron donating substituents such as methyl group) may exist on the benzene ring on which $R^1$ substitutes. It is preferred that $R^1$ represents one cyano group binding at the para-position to the dicarbonyl group. In this case, it is preferred that any substituent other than $R^1$ does not exist on the benzene ring.

$R^2$ and $R^3$ independently represent a hydrogen atom or a halogen atom, and it is preferred that $R^2$ and $R^3$ are hydrogen atoms. $R^4$ and $R^5$ independently represent a hydrogen atom, an alkylcarbonyl group, or an alkylcarbonyloxymethyl group. As the alkyl moiety of the alkylcarbonyl group or the alkylcarbonyloxymethyl group, a linear or branched $C_{1-6}$ alkyl group is preferred. It is preferred that $R^4$ and $R^5$ are hydrogen atoms. Re represents a hydrogen atom or an alkyl group. As the alkyl moiety, a linear or branched $C_{1-6}$ alkyl group is preferred. As $R^6$, hydrogen atom is preferred.

In the benzene ring bound to the xanthene ring, although the binding position of the dicarbonyl group to which the phenyl group having at least one substituent $R^1$ binds is not particularly limited, it is preferred that the dicarbonyl group is in the para-position to the xanthene ring.

The compounds of the present invention represented by the aforementioned general formula (IA) or (IB) can exist as an acid addition salt or a base addition salt. Examples of the acid addition salt include mineral acid salts such as hydrochlorides, sulfates, and nitrates, and organic acid salts such as methanesulfonates, p-toluenesulfonates, oxalates, citrates, and tartrates. Examples of the base addition salt include metal salts such as sodium salts, potassium salts, calcium salts, and magnesium salts, ammonium salts, and organic amine salts such as triethylamine salts. In addition to these examples, salts of amino acids such as glycine may be formed. The compounds and salts thereof according to the present invention may exist as hydrates or solvates, and any of these substances falls within the scope of the present invention.

The compounds of the present invention represented by the general formula (IA) or (IB) may have one or more asymmetric carbons depending on the types of the substituents. Stereoisomers such as optically active substances based on one or two or more asymmetric carbons and diastereoisomers based on two or more asymmetric carbons, as well as arbitrary mixtures of the stereoisomers, racemates and the like all fall within the scope of the present invention. When $R^6$ is a hydrogen atom, the carboxyl group may form a lactone, and such structural isomers also fall within the scope of the present invention. A compound represented by the general formula (IA) in which $R^4$ is a hydrogen atom and a compound represented by the general formula (IB) in which $R^6$ is a hydrogen atom are tautomers. Those skilled in the art would readily recognize the existence of such tautomers, and any of these tautomers also fall within the scope of the present invention.

Methods for preparing typical compounds of the present invention are specifically shown in detail in the examples of this specification. Accordingly, those skilled in the art can prepare any of the compounds according to the present invention represented by the aforementioned general formulae by suitably choosing starting reaction materials, reaction conditions, reaction reagents and the like on the basis of the explanations in the examples, and modifying or altering these methods as required. In addition, the fluorescein derivatives such as 4-aminofluorescein, which can be used as starting compounds, can be prepared by the methods described in, for example, "Yuuki Gousei Kagaku (Synthetic Organic Chemistry) IX," (Tetsuji Kametani, Nankodo Co., Ltd., p. 215 (1977)), and the like.

The term "measurement" used in the present specification should be construed in its broadest sense, including quantification, qualification, measurements performed for the purpose of diagnosis, tests, detections and the like. The method for measuring hydrogen peroxide of the present invention generally comprises (A) the step of reacting the aforementioned reagent with hydrogen peroxide, and (B) the step of measuring fluorescence of a decomposition product of the aforementioned reagent generated in the aforementioned step (A). The compounds represented by the aforementioned general formula (IA) or (IB) themselves are non-fluorescent or weakly fluorescent, but when they are brought into contact with hydrogen peroxide, they are decomposed by the action of hydrogen peroxide to generate strongly fluorescent 5-carboxyfluorescein.

The reagent for measuring hydrogen peroxide of the present invention has a property that the reagent specifically reacts with hydrogen peroxide among the various active oxygen species, i.e., hydroxyl radical, peroxynitrite, hypochlorite ion, nitrogen monoxide, hydrogen peroxide, superoxide anion, singlet oxygen, and the like, and is a reagent that enables specific measurement of hydrogen peroxide.

Although the means for fluorescent measurement using the reagent of the present invention is not particularly limited, a method of measuring fluorescence spectra in vitro, a method of measuring fluorescence spectra in vivo using a bioimaging technique, or the like can be used. For example, when quantitative analysis is performed, it is desirable to create a calibration curve beforehand in a conventional manner. If the reagent of the present invention is introduced into cells by microinjection or the like, hydrogen peroxide localizing in individual cells can be measured in real time with high sensitivity by a bioimaging technique, and if the reagent is used in cell culture mixture, culture medium or a perfusate for tissue sections and the like, hydrogen peroxide released from the cells or biological tissues can be measured. By using the reagent of the present invention, behaviors of hydrogen peroxide in cells or biological tissues can be measured in real time, and thus the reagent can be preferably used for cause investigation of disease pathologies, development of therapeutic agents, and the like.

The reagent of the present invention may also be used as a composition formulated with additives ordinarily used for preparation of reagents, if desired. For example, as additives for use of the reagent in a physiological condition, such additives as dissolving aids, pH modifiers, buffers, isotonic agents and the like can be used, and amounts of these additives can suitably be chosen by those skilled in the art. The compositions may be provided as compositions in appropriate forms, for example, powdery mixtures, lyophilized products, granules, tablets, solutions, and the like.

EXAMPLES

The present invention will be more specifically explained with reference to examples. However, the scope of the present invention is not limited to the following examples.

Example 1

[Formula 2]

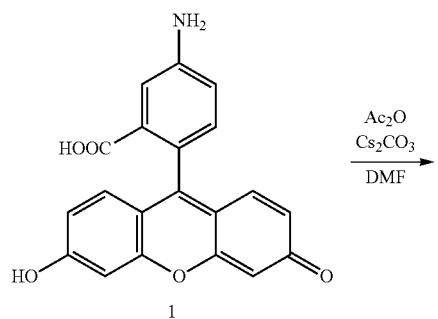

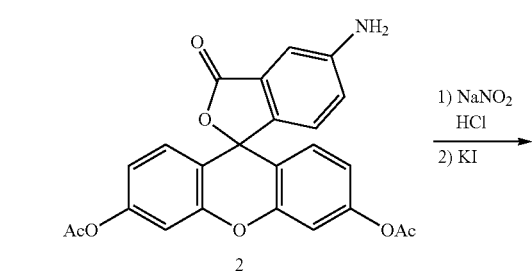

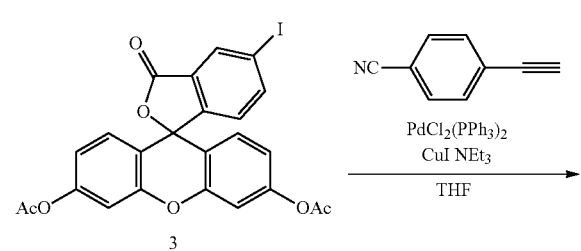

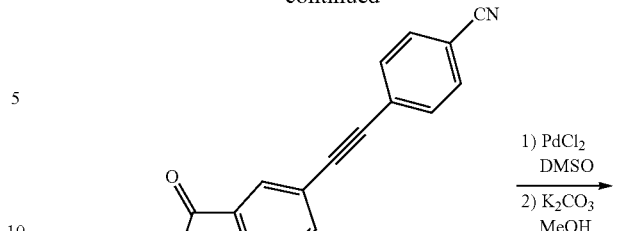

(1) Synthesis of 5-(4-cyanophenylethynyl)fluorescein diacetate (4)

Compound 3 was synthesized with reference to J. Org. Chem., 2003, 68, 8264-8267. Compound 3 (280 mg, 0.516 mmol), 4-ethynylbenzonitrile (80 mg, 0.629 mmol), dichlorobis(triphenylphosphine)palladium (22.8 mg, 0.0325 mmol), and copper iodide (28.4 mg, 0.149 mmol) were suspended in tetrahydrofuran (THF, 20 ml), triethylamine (0.27 ml, 1.95 mmol) was added to the suspension, and the reaction mixture was stirred at room temperature for 12 hours under an argon atmosphere. The solvent was evaporated under reduced pressure, and the obtained solid was purified by silica gel column chromatography to obtain the objective compound (216 mg, 0.399 mmol, yield: 74%).

(2) Synthesis of 5-(4-cyanobenzoyl)carbonylfluorescein (5)

Compound 4 (72.4 mg, 0.137 mmol) was dissolved in dimethyl sulfoxide (DMSO, 1 ml), palladium chloride (4.37 mg, 0.0246 mmol) was added to the solution, and the reaction mixture was stirred at 100° C. for 10 hours under an argon atmosphere. The reaction mixture was cooled to room temperature, then methanol (10 ml) and potassium carbonate (100 mg) were added the reaction mixture, and the mixture was stirred at room temperature for 30 minutes. Methanol in the reaction mixture was evaporated under reduced pressure, and the residue was neutralized by adding 2 N hydrochloric acid, and then purified by preparative HPLC to obtain the objective substance (32.0 mg, 0.0654 mmol, yield: 48%).

$^1$H NMR (300 MHz, DMSO-ds) δ 10.1 (s, 1H), 8.50 (m, 1H), 8.37 (d, 1H, J=8.07 Hz), 8.20 (d, 2H, J=8.25 Hz), 8.10 (d, 2H, J=8.07 Hz), 7.51 (d, 1H, J=8.04 Hz), 6.69 (d, 2H, J=1.65 Hz), 6.63 (d, 2H, J=8.61 Hz), 6.54 (dd, 2H, J=8.79, 1.65 Hz)

$^{13}$C NMR (100 MHz, DMSO-ds) δ 191.2, 190.7, 167.5, 159.8, 157.8, 151.8, 136.7, 135.5, 133.8, 133.0, 130.8, 129.3, 127.0, 125.1, 118.0, 116.8, 112.8, 108.5, 102.3

HRMS (ESI−) Calcd for [M-H], 488.07703. Found, 488.07359 (−3.43 mmu)

Example 2

Compound 5 shows fluorescence quenched by the photo-induced electron transfer (PeT) mechanism from the xanthene ring to the benzyl structure, and this compound itself is weakly fluorescent. However, upon reaction with hydrogen peroxide, the compound generates strongly fluorescent 5-carboxyfluorescein.

[Formula 3]

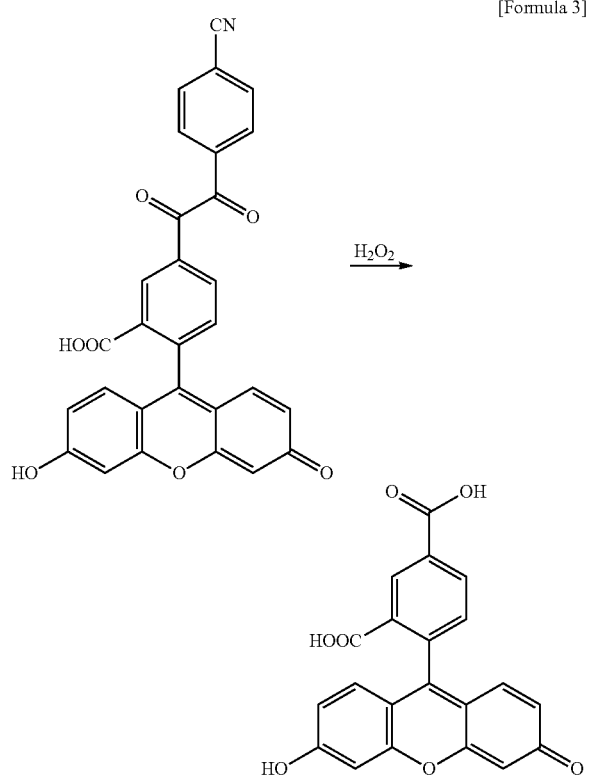

FIG. 1 (A) shows the change of the fluorescence spectrum (excitation wavelength: 490 nm) over time (after 5, 15, 30, and 60 minutes) observed when adding hydrogen peroxide (100 μM) to Compound 5 (1 μM). FIG. 1 (B) shows relative fluorescence intensities at 520 nm (excitation wavelength: 490 nm) observed when adding hydrogen peroxide (100 μM, for 30 minutes), hydroxyl radical (10 μM), peroxynitrite (10 μM), hypochlorite ion (10 μM), NOC13 (100 μM) as a nitrogen monoxide generator, and EP-1 (3-(1,4-dihydro-1,4-epidioxy-1-naphthyl)propionic acid, 100 μM) as a singlet oxygen generator to Compound 5 (1 μM), respectively. The addition of hydroxyl radical (10 μM) to the test system was performed by the method of adding hydrogen peroxide (10 μM) to a solution of Compound 5, and then immediately adding a solution of iron(II) perchlorate (10 μM) in purified water to the mixture to generate hydroxyl radicals by the Fenton reaction. FIG. 1 (C) shows relative fluorescence intensities at 520 nm (excitation wavelength: 490 nm) observed when superoxide (10 μM) was reacted with Compound 5 (10 μM) using a hypoxanthine/xanthine oxidase (HPX/x.o.) system prepared by adding xanthine oxidase (x.o., 2.38 mUnit/L) and hypoxanthine (HPX, 10 μM), by performing such a reaction as mentioned above with further adding super oxide dismutase (SOD, 60 Unit/L) to the HPX/x.o. system, and by performing such a reaction as mentioned above with adding catalase (100 Unit/L) instead of SOD to the HPX/x.o. system.

(A) When hydrogen peroxide was added to Compound 5, increase of fluorescence intensity was observed over time.

(B) In comparison of the cases where hydrogen peroxide, hydroxyl radical, peroxynitrite, hypochlorite ion, NOC13, or EP-1 was added to Compound 5, it was confirmed that increase of fluorescence intensity was observed only when hydrogen peroxide was added, and the addition of the other reactive oxygen species gave no increase of fluorescence intensity.

(C) When superoxide was reacted with Compound 5, the fluorescence intensity observed was higher in the case using the HPX/x.o. system than in the case of the control (Hnon). Even when SOD was added to the HPX/x.o. system, there was no significant change in the degree of the increase of fluorescence intensity. On the other hand, the addition of catalase suppressed the increase of fluorescence intensity, and the fluorescence intensity was reduced to around the level of the control (Hnon). On the basis of these results, it was considered that the increase of the fluorescence intensity observed with the HPX/x.o. system was induced by hydrogen peroxide as a disproportionation reaction product of superoxide. From the above results, it was concluded that Compound 5 of the present invention had a property as a hydrogen peroxide-specific fluorescent probe, and the compound was usable as a reagent for measuring hydrogen peroxide. From the results obtained by adding catalase to the HPX/x.o. system, it was confirmed that the compound of the present invention can also be used for measuring the activity of catalase.

Example 3

Figure 2:
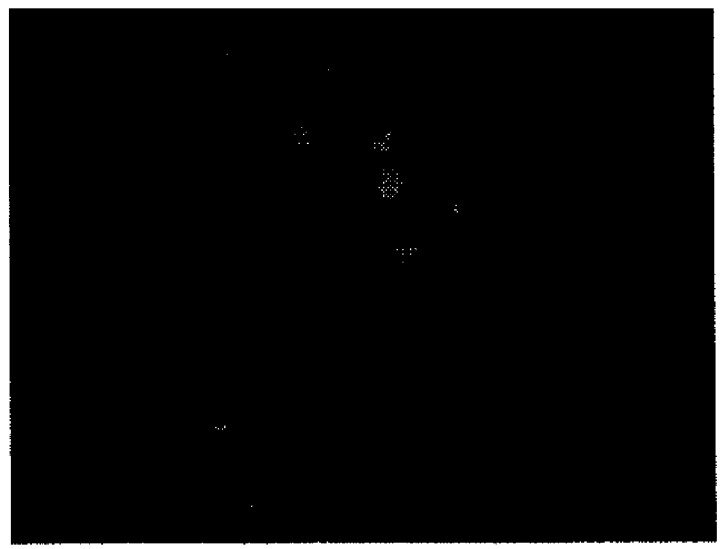
FIG. 2 shows the results of fluorescent images of the RAW264.7 cells: A) without stimulation, and B) with a lipopolysaccharide (LPS) and interferon-γ (IFN-γ) stimulation. The excitation wavelength is 470 to 495 nm and the fluorescence wavelength is 510 to 550 nm.
Figure 2:
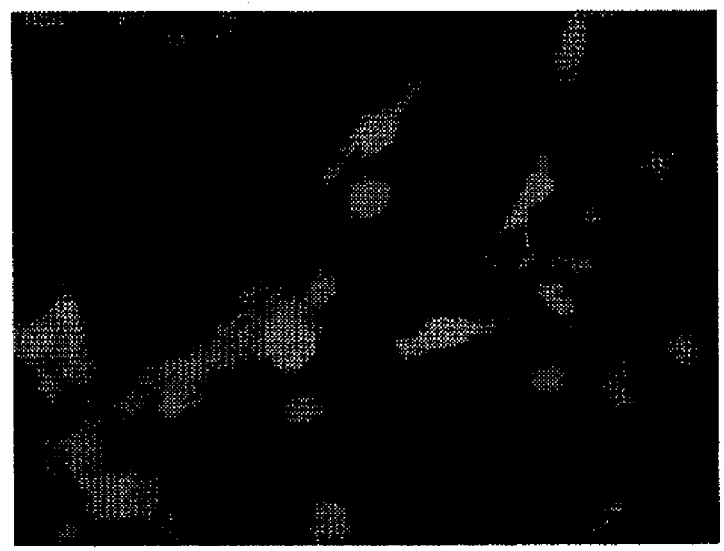

It was confirmed that Compound 5 was also usable for detection of hydrogen peroxide in live cells. The RAW264.7 cells were stimulated with a lipopolysaccharide (LPS, 50 μg/ml) and interferon-γ (IFN-γ, 100 unit/ml) for 12 hours, then a diacetylated compound of Compound 5 was loaded on the cells, and 2 hours later, the cells were observed under a fluorescence microscope using the U-MNIBA2 filter set produced by Olympus Corporation (excitation wavelength: 470 to 495 nm, fluorescence wavelength: 510 to 550 nm) (FIG. 2). The fluorescence intensity observed was higher when loading Compound 5 on the stimulated cells (B) than on the non-stimulated cells (A).

INDUSTRIAL APPLICABILITY

The reagent for measuring hydrogen peroxide provided by the present invention has a property that the reagent specifically reacts with hydrogen peroxide among various active oxygen species to emit strong fluorescence, and thus enables specific measurement of hydrogen peroxide with high sensitivity. Therefore, the reagent is useful for visualizing behaviors of hydrogen peroxide in living organisms.

What is claimed is:

1. A compound represented by the following formula (IA) or (IB):

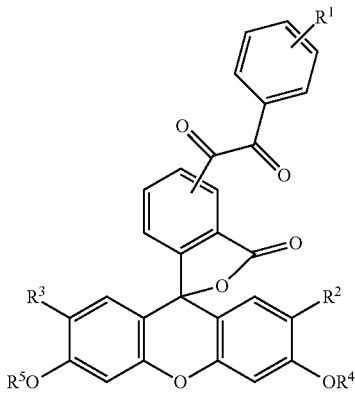 (IA)

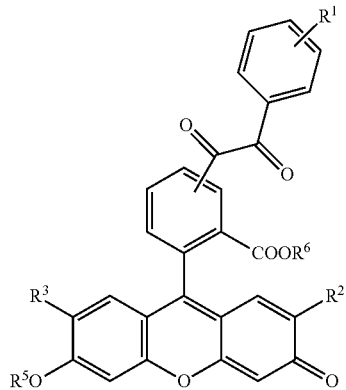 (IB)

wherein $R^1$ represents one or two or more electron withdrawing substituents existing on the benzene ring, $R^2$ and $R^3$ independently represent a hydrogen atom or a halogen atom; $R^4$ and $R^5$ independently represent a hydrogen atom, an alkylcarbonyl group, or an alkylcarbonyloxymethyl group, and $R^6$ represents a hydrogen atom or an alkyl group, or a salt thereof.

2. The compound or a salt thereof according to claim 1, wherein $R^1$ represents one cyano group, halogen atom, carboxy group, or sulfo group on the benzene ring, $R^2$ and $R^3$ are hydrogen atoms, $R^4$ and $R^5$ are hydrogen atoms, and $R^6$ is a hydrogen atom.

3. The compound or a salt thereof according to claim 1, wherein, in the benzene ring bound to the xanthene ring, the binding position of the dicarbonyl group to which the phenyl group having at least one substituent $R^1$ binds is the para-position to the xanthene ring.

4. A reagent for measuring hydrogen peroxide, which comprises a compound represented by the formula (IA) or (IB) according to claim 1 or a salt thereof.

5. A method for measuring hydrogen peroxide, which comprises the following steps: (A) reacting the reagent according to claim 4 with hydrogen peroxide, and (B) measuring fluorescence of a decomposition product of the reagent generated in the step (A).

* * * * *